United States Patent [19]

DuCharme

[11] 3,968,211
[45] July 6, 1976

[54] COMPOSITIONS AND METHODS OF USE OF AMIDINES FOR ANTI-ARRHYTHMIC PURPOSES

[75] Inventor: Donald W. DuCharme, Cooper Township, Kalamazoo County, Mich.

[73] Assignee: The Upjohn Company, Kalamazoo, Mich.

[22] Filed: Feb. 11, 1974

[21] Appl. No.: 441,383

[52] U.S. Cl. .............................. 424/248; 424/246; 424/250; 424/267
[51] Int. Cl.² ............. A61K 31/535; A61K 31/54; A61K 31/445
[58] Field of Search ................ 424/246, 248, 267; 260/247, 293

[56] References Cited
UNITED STATES PATENTS 3,697,505    2/1969    Gubitz ............................... 424/248
3,728,389    4/1973    Hudson et al. .................. 260/564 R

*Primary Examiner*—Stanley J. Friedman
*Assistant Examiner*—Daren M. Stephens
*Attorney, Agent, or Firm*—Martin B. Barancik; Roman Saliwanchik

[57]    ABSTRACT

Compounds of the formula below are compounded into pharmaceutical compositions and are useful for treatment of arrhythmic conditions.

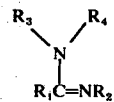

14 Claims, No Drawings

COMPOSITIONS AND METHODS OF USE OF AMIDINES FOR ANTI-ARRHYTHMIC PURPOSES

BRIEF DESCRIPTION OF THE INVENTION

It has been discovered that the compounds of FIG. I are useful in the treatment of arrhythmic situations in mammals. Additionally, the compounds of this invention show diuretic activity. The compounds are formulated with pharmaceutical carriers for oral and parenteral means of administration for anti-arrhythmic and diuretic uses.

DETAILED DESCRIPTION OF THE INVENTION

In accordance with this invention, there is provided a method for treating arrhythmic situations in mammals which comprises systemically administering to said mammals a compound

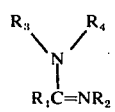

(1)

wherein $R_1$ and $R_2$ are the same or different and are selected from the group consisting of alkyl of one to eight carbon atoms, inclusive, cycloalkyl of from five to eight carbon atoms, inclusive, adamantyl, phenyl, phenalkyl, where alkyl is from one to three carbon atoms, inclusive, and mono and di-substituted phenyl and phenyl moiety of phenalkyl wherein the substituents are the same or different and are selected from the group consisting of alkyl from one to three carbon atoms, inclusive, alkoxy of from one to three carbon atoms, inclusive, halogen, and trifluoromethyl.

$R_3$ and $R_4$ are the same or different and are selected from the group consisting of alkyl of from one to six carbon atoms, inclusive, cycloalkyl of from five to eight carbon atoms, phenyl, phenalkyl, where alkyl is from one to three carbon atoms, inclusive, mono-substituted phenyl and phenyl moiety of phenalkyl wherein the substituent is selected from the group consisting of alkyl of one to three carbon atoms, inclusive, alkoxy of one to three carbon atoms, inclusive, halogen, and trifluoromethyl, and when $R_3$ and $R_4$ are taken together with the nitrogen atom to which they are attached, form a saturated heterocyclic ring,

wherein Z is selected from the group consisting of methylene, N—A where N is nitrogen and A is hydrogen or alkyl of one to three carbon atoms, inclusive, oxygen and sulfur and wherein Z is methylene,

has from four to six ring carbon atoms and when Z is N—A where N and A are as defined above, oxygen and sulfur,

is, respectively, piperazino, N-alkylpiperazino, morpholino and thiomorpholino, and pharmaceutically acceptable acid addition salts thereof in association with a pharmaceutical carrier.

Another group of compounds of the invention are where $R_1$ and $R_2$ are the same or different and are selected from the group consisting of alkyl of from four to six carbon atoms, inclusive, cycloalkyl of five to seven carbon atoms, inclusive, adamantyl, phenyl, and phenalkyl wherein alkyl is from one to three carbon atoms, inclusive;

$R_3$ and $R_4$, taken together with the nitrogen atom to which they are attached, form a saturated heterocyclic ring,

wherein Z is selected from the group consisting of methylene, N—A as previously defined, oxygen and sulfur, and when Z is methylene,

is from four to six carbon atoms, inclusive, and when Z is N—A, as previously defined, oxygen or sulfur, then

is, respectively, piperazino, N-alkylpiperazino, morpholino, and thiomorpholino.

A further group of compounds of the invention are where $R_1$ and $R_2$ are the same or different and are selected from the group consisting of cycloalkyl of five to seven carbon atoms, inclusive, and adamantyl;

$R_3$ and $R_4$, when taken together with the nitrogen atom to which they are attached, form a saturated heterocyclic ring,

wherein Z is selected from the group consisting of methylene, N—A as previously defined, oxygen, and sulfur, and then

is, respectively, piperidino, piperazino, N-alkylpiperazino, morpholino, and thiomorpholino.

Preferred compounds are N-(N,2-dicyclohexylacetimidoyl)morpholine and its nitrate salt, N-[p-chloro-N-cyclohexylbenzimidoyl]morpholine and its hydrochloride salt and N-(N,1-dicyclohexylformimidoyl)morpholine and its nitrate salt.

As employed in the above disclosure and throughout the specification, the term "halogen" includes fluorine, chlorine, bromine, and iodine. The term "alkyl" includes methyl, ethyl, propyl and isomers thereof, when limited to three carbon atoms. When limited to a higher number of carbon atoms, the term encompasses compounds through that number of carbon atoms and isomers thereof. "Cycloalkyl" of five to eight carbon atoms, inclusive, includes cyclopentyl, cyclohexyl, cycloheptyl and cyclooctyl. "Pharmaceutically acceptable acid addition salts" include the hydrochloric, hydrobromic, hydriodic, nitric, sulfuric, phosphoric, acetic, lactic, citric, succinic, benzoic, salicylic, palmitic, cyclohexanesulfamic and the like.

The compounds employed in the method of treating arrhythmic conditions can be prepared by methods known in the art. For example, methods of preparation are outlined by H. Soll in Houben-Weyl's "Methoden der organischen chemie", 4th ed. Vol. XI, Part 2, 1958, p. 39, and additionally, H. Eilingsfeld et al., Angew. Chem., 72, 836 (1960).

Compounds illustrative of the scope of the invention for treating arrhythmic conditions are below:

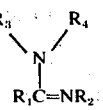

TABLE 1

| $R_1$ | $R_2$ | $R_3$ | $R_4$ |
|---|---|---|---|
| 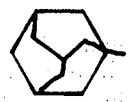 |  | 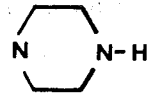 | |
|  |  | 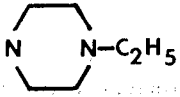 | |
|  |  | 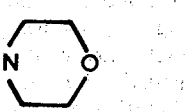 | |
|  | 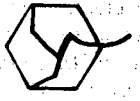 | 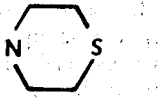 | |
|  | 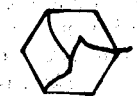 | 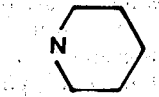 | |
| 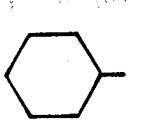 | 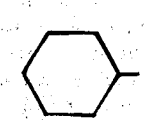 | 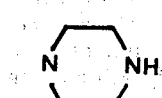 | |
|  | 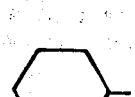 | 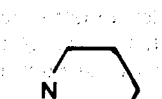 | |
| 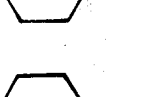 | 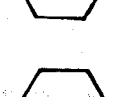 | 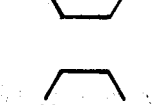 | |
| 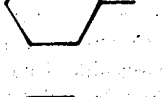 |  | 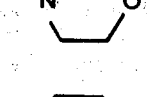 | |
| 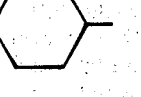 |  | 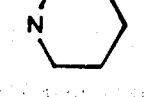 | |
| 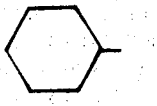 |  | 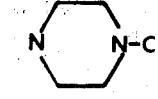 | |
| 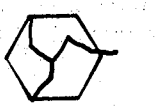 | 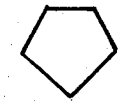 | 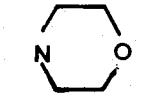 | |

| R₁ | R₂ | R₃ | R₄ |
|---|---|---|---|
| 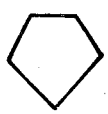 |  |  | |
| 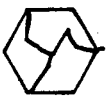 |  | 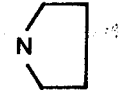 | |
| 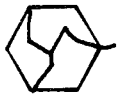 | 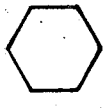 | 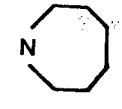 | |
| 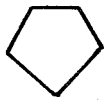 | 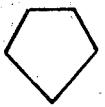 | 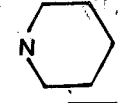 | |
| 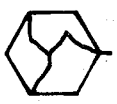 |  | 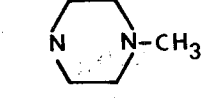 | |
|  |  | 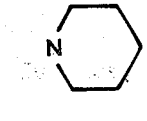 | |
| 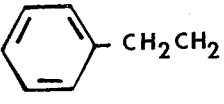 |  |  | |
|  | 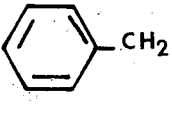 | 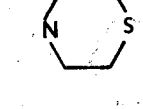 | |
| $iC_6H_{13}$ | $C_4H_9$ | $CH_3$ | $iC_5H_{11}$ |
| $tC_4H_9$ | $C_5H_{11}$ | 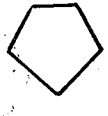 | $C_2H_5$ |
| $iC_6H_{13}$ | $C_4H_9$ | $C_2H_5$ | 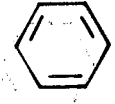 |
| $iC_4H_9$ | $C_6H_{13}$ | $C_4H_9$ | 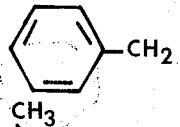 |
| $tC_6H_{13}$ | $iC_5H_{11}$ | $iPr$ | 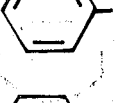 |
| $C_5H_{11}$ | $CH_3$ | $CH_3$ |  |

| R₁ | R₂ | R₃ | R₄ |
|---|---|---|---|
| C₂H₅ | iC₄H₉ | C₄H₉ | 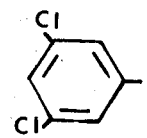 |
| C₃H₇ | C₅H₁₁ | C₂H₅ | 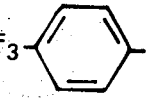 |
| CH₃ | C₄H₉ | C₅H₁₁ | 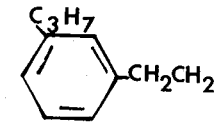 |
| C₆H₁₃ | C₃H₇ | C₃H₇ | 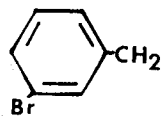 |
| C₆H₁₃ | C₆H₁₃ |  | |
| C₆H₁₃ | C₄H₉ |  | |
| C₆H₁₃ | 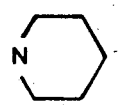 |  | |
|  |  | CH₃ | C₆H₁₃ |
|  |  | C₂H₅ | C₅H₁₁ |
| 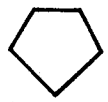 |  |  | C₂H₅ |
|  |  |  | |
| 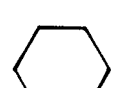 | 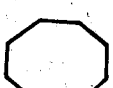 |  | C₃H₇ |
| 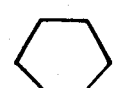 | 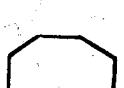 |  | 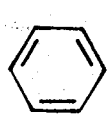 |

| R1 | R2 | R3 | R4 |
|---|---|---|---|
| 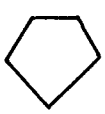 | 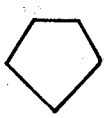 | 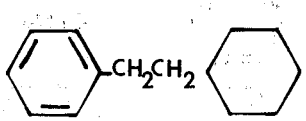 |  |
| 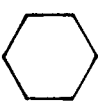 | 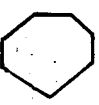 | C4H9 | 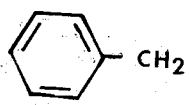 |
| 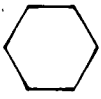 |  | 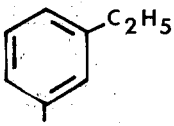 | CH3 |
| 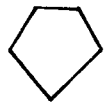 |  | 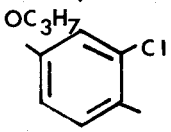 | 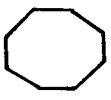 |
| 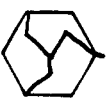 |  | |  |
| 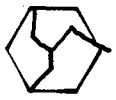 |  | C3H7 |  |
|  |  | 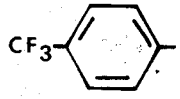 | 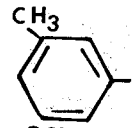 |
| 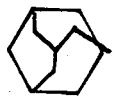 |  | 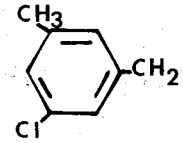 | 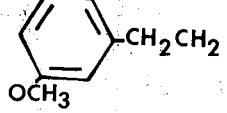 |
|  | 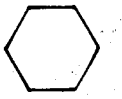 | |  |
| |  | 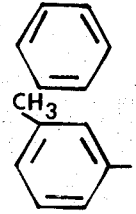 | 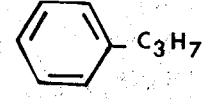 |
| C4H9 | 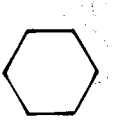 | C2H5 | 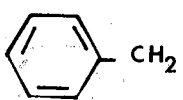 |
| 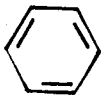 |  | | 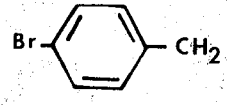 |
|  | 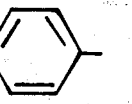 | 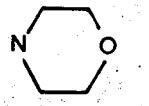 | |
| C2H5 |  | 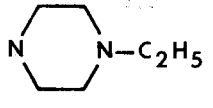 | |

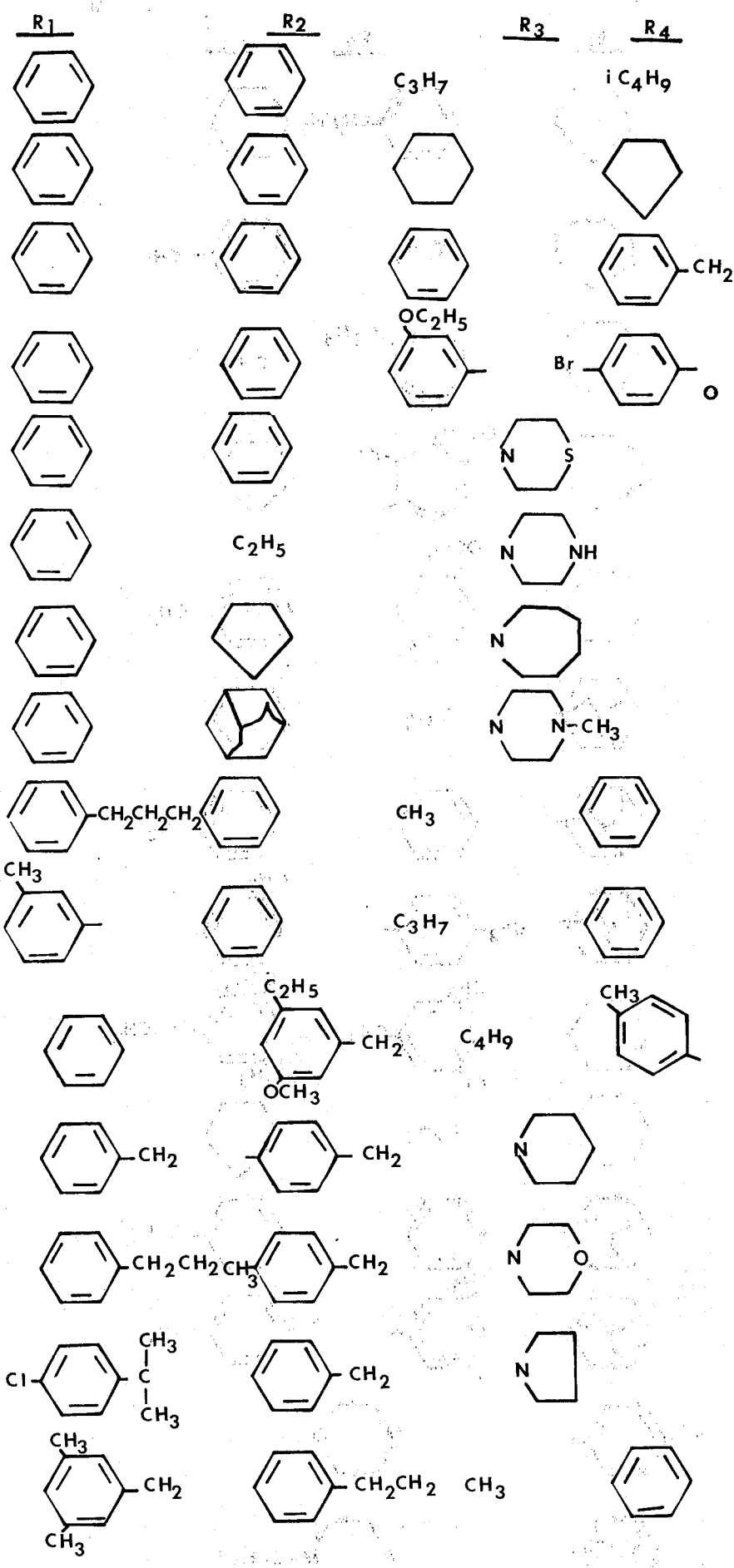

| R1 | R2 | R3 | R4 |
|---|---|---|---|

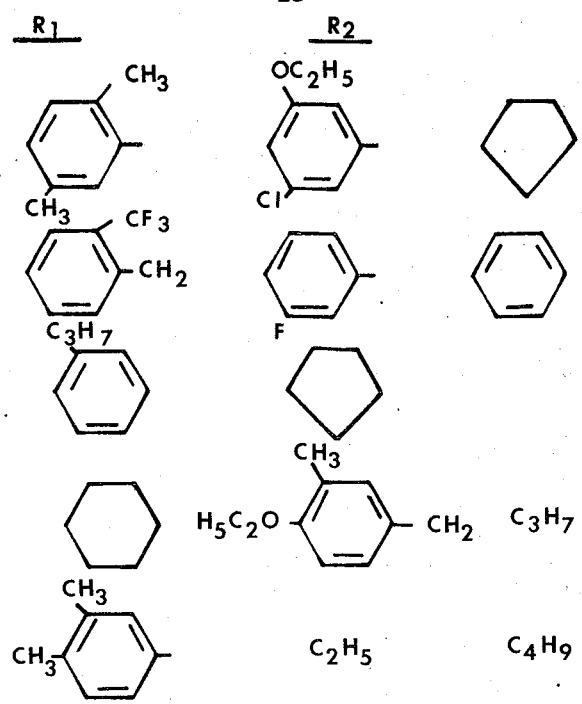
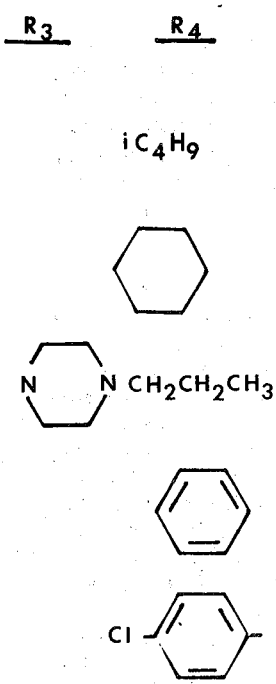

Following are specific compounds within the invention and the methods of preparing them. These examples are not intended to be limitations on the broad scope of the invention, but merely illustrative.

EXAMPLE 1

N-(N,2-Dicyclohexylacetimidoyl)morpholine nitrate

The N-cyclohexylcyclohexaneacetamide is prepared from cyclohexylacetyl chloride (from 10 gm. of cyclohexylacetic acid and 50 ml. of thionyl chloride, 45 minutes at reflux) in 50 ml. of dry benzene added to 14 gm. of cyclohexylamine in 100 ml. of benzene over ten minutes. The reaction is stirred at reflux for one hour, cooled and diluted with methylene chloride. The organic layer is washed with dilute hydrochloric acid, then water and sodium bicarbonate solution, dried and concentrated. Product is recrystallized from alcohol water: 11.8 gm. (76%), m.p. 164°–165°.

The N-cyclohexylcyclohexaneacetamide (9 gm., 0.04 mole) is added in one portion to 5 gm. (0.05 mole) of phosgene in 100 ml. of cold tetrahydrofuran. Reaction is stirred at room temperature for sixteen hours, solvent evaporated in vacuo and residue dissolved in 50 ml. of chloroform. This solution is added to a solution of 15 gm. of morpholine in 50 ml. of acetonitrile at 0°–10° for 20 minutes, than at room temperature for two hours, followed by reflux for 2.5 hours. Solvent is evaporated and residue treated with cold dilute sodium hydroxide solution. It is extracted with ether and the ether is dried over $K_2CO_3$ and evaporated. The residue is dissolved in pentane, filtered and the pentane is concentrated, residue diluted with toluene and concentrated to remove residual morpholine. The residue is converted to the nitrate salt in ether. The nitrate is recrystallized from acetonitrile-ether: 7.0 g., (49%), m.p. 196°–197°.

Analysis Calcd. for: $C_{18}H_{32}N_2O \cdot HNO_3$; C, 60.82; H, 9.36; N, 11.82 Found: C, 60.87; H, 9.33; N, 11.85

EXAMPLE 2

N-(p-Chloro-N-cyclohexylbenzimidoyl)-morpholine hydrochloride a. N-Cyclohexyl-p-chlorobenzamide Cyclohexylamine (80 gm., 0.8 mole) is dissolved in 2.5 l. of benzene and treated dropwise with 70 gm. (0.4 mole) of p-chlorobenzoyl chloride in 250 ml. of benzene over 45 minutes with intermittent cooling to maintain reaction temperature between 22°–30°. After stirring an additional 15 minutes, the mixture is diluted with benzene and washed with water. A suspended solid is filtered and the filtrate concentrated to 1 l. to give a second crop; these are combined and recrystallized from methanol, 65.0 gm. (68.5%), m.p. 191°–193°.

b. Product

To a cold solution of 9.6 gm. (0.096 mole) of phosgene in tetrahydrofuran is added in one portion 19.0 gm. (0.08 mole) of N-cyclohexyl-p-chlorobenzamide. After ten minutes the reaction mixture is allowed to warm to room temperature, stirred overnight, and the mixture concentrated to a solid in vacuo with a bath temperature of 30°. The crude residue is suspended in 250 ml. of acetonitrile, cooled to 0° and treated with a solution of 28.0 gm. (0.32 mole) of morpholine in 100 ml. of acetonitrile. After allowing the reaction mixture to warm to room temperature it is heated at reflux for two hours, concentrated in vacuo to an oil and suspended in ether. A precipitate is collected and shown to be starting material. The filtrate is concentrated in vacuo, the residue taken up in acetone and treated with excess dry HCl in ether. Ether is added to the cloud point and the mixture cooled to give 3.7 gm. (13.5%) m.p. 278°–279°.

Analysis Calcd. for: $C_{17}H_{23}ClN_2O \cdot HCl$ C, 59.47; H, 7.05; N, 8.16, Cl, 20.66 Found: C, 59.20; H, 7.04; N, 7.86; Cl, 19.83

EXAMPLE 3

N-(N,1-Dicyclohexylformimidoyl)morpholine nitrate a. N,1-Dicyclohexylcarboxamide A solution of 58.8 gm. (0.4 mole) of cyclohexanecarbonyl chloride in 200 ml. of benzene is added dropwise to 80 gm. (0.8 mole) of cyclohexylamine in 1 l. of benzene with periodic cooling to maintain the reaction mixture between 22° and 30°. After stirring the mixture an additional fifteen minutes, the solid is filtered off, the filtrate washed with water and dried over $Na_2SO_4$.

The solution is concentrated in vacuo to a solid which is crystallized from 2-propanol-water. The solid which has been filtered from the reaction mixture is suspended in 1500 ml. of benzene, the solution washed with water, dried over Na₂SO₄, concentrated to a solid and recrystallized from 2-propanol-water. The combined yield is 61.5 gm. (74%), m.p. 170°–173°, (lit. m.p. 172°–173°).

b. Product

To a cold solution of 3.0 g. (0.03 mole) of phosgene in tetrahydrofuran is added in one portion 5.0 g. (0.024 mole) of N,1-dicyclohexylcarboxamide and the mixture stirred one hour in the cold. The mixture is stirred at room temperature overnight, the solvent evaporated off in vacuo at 30° and the residue suspended in 200 ml. of acetonitrile. To this cooled suspension is added 6 g. of morpholine in acetonitrile, stirred in cold for one-half hour, at room temperature for two hours, and at reflux for two hours. The solvent is evaporated in vacuo and the residue suspended in dilute HCl, washed with ether, made basic with 2N NaOH and extracted with ether. The combined ether extracts are dried over Na₂SO₄ and the filtrate concentrated in vacuo; toluene is added to the residue and stripped off in vacuo. The residue is taken up in ether and treated with 70% nitric acid in ethanol, the solvent evaporated in vacuo and the resultant oil crystallized from ethanol-ether. Recrystallization from acetonitrile-ether gives 2.9 g. (35%), m.p. 173°–175° foam.

Analysis Calcd. for: $C_{17}H_{30}N_2O \cdot HNO_3$ C, 59.80; H, 9.15; N, 12.31 Found: C, 59.46; H, 9.23; N, 12.13

The compounds are presented for administration to humans and animals in unit dosage forms of pharmaceutical compositions such as tablets, capsules, pills, powders, granules, sterile parenteral solutions or suspensions, and oil-in-water or water-in-oil emulsions and suppositories containing suitable quantities of the compound.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

A rectal suppository can be employed to deliver the active compound where the mammal cannot be treated conveniently by means of other dosage forms, such as orally, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The term "unit dosage form" as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, powder packets, wafers, granules, cachets, teaspoonsful, tablespoonsful, droppersful, ampuls, vials, suppositories, segregated multiples of any of the foregoing and other forms as herein described.

The administration of the compositions to mammals brings about cardioregulatory action. Arrhythmias such as auricular fibrillation, ventricular fibrillation, paroxysmal atrial or ventricular tachycardia and the like can be treated through this invention. Additionally, the compounds within this application are useful as diuretics. As such, they have the property of augmenting urine volume and sodium excretion. This effect is of particular significance when the mammal suffering cardiac abnormalities, for example, arrhythmia, also has a build-up of bodily fluids.

For treating cardioregulatory problems such as arrhythmia, an effective dosage of the particular compound is employed. The particular dosage of the selected compound for treatment depends on the route of administration and the potency of the compound, as well as the size, weight and sex of the particular mammal. For orally or rectally treating arrhythmia in mammals, the dosage is from about 10 to about 1000 mg. per day in one to four equally divided doses. A preferred dosage range is from about 40 to about 400 mg. per day. Diuresis can be observed in a range of about 1 to about 1000 mg. per day, preferably 10 to 500 mg. per day. For treating arrhythmia in mammals parenterally, the dosage is from about 1 to about 500 mg. per day in one to four equally divided doses. A preferred dosage range is from about 10 to about 200 mg. per day. Diuresis can be observed in the range of from about 1 to about 500 mg. per day, preferably 10 to about 200 mg. parenterally.

EXAMPLE 4

A lot of 10,000 tablets, each containing 100 mg. of N-(N,2-dicyclohexylacetimidoyl)morpholine nitrate is prepared from the following types and amounts of ingredients:

| | |
|---|---|
| N-(N,2-dicyclohexylacetimidoyl)morpholine nitrate | 1,000 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in treating auricular fibrillation in man at a dose of 1 tablet 4 times a day.

EXAMPLE 5

One thousand two-piece hard gelatin capsules, each containing 10 mg. of N-(p-chloro-N-cyclohexylbenzimidoyl)morpholine hydrochloride are prepared from the following types and amounts of ingredients:

| | |
|---|---|
| N-(p-chloro-N-cyclohexylbenzimidoyl)morpholine hydrochloride | 10 Gm. |
| Dicalcium phosphate | 150 Gm. |
| Talc | 15 Gm. |
| Magnesium stearate | 1 Gm. |

The ingredients are mixed well and filled into capsules of the proper size.

Capsules so prepared are useful in preventing paroxysmal atrial tachycardia at a dose of one capsule every four hours.

EXAMPLE 6

One thousand tablets, each containing 300 mg. of N-(N,1-dicyclohexylformimidoyl)morpholine nitrate are prepared from the following types and amounts of ingredients:

| | |
|---|---|
| N-(N,1-dicyclohexylformimidoyl)morpholine nitrate | 300 Gm. |
| Microcrystalline cellulose NF | 410 Gm. |
| Starch | 100 Gm. |
| Magnesium stearate powder | 4 Gm. |

The ingredients are screened and blended together and pressed into 814 mg. tablets The tablets are useful in treating auricular fibrillations in man at a dose of one tablet 3 times a day.

EXAMPLE 7

One thousand tablets, each containing 125 mg. of N-(N,2-dicyclohexylacetimidoyl)morpholine nitrate are prepared from the following types and amounts of ingredients:

| | |
|---|---|
| N-(N,2-dicyclohexylacetimidoyl)morpholine nitrate | 125 Gm. |
| Microcrystalline cellulose NF | 410 Gm. |
| Starch | 100 Gm. |
| Magnesium stearate powder | 3 Gm. |

The ingredients are screened and blended together and pressed into 638 mg. tablets.

The tablets are useful in treating paroxysmal ventricular tachycardia and an increased fluid retention at a dose of four tablets per day.

EXAMPLE 8

A sterile preparation suitable for intramuscular injection and containing 25 mg. of N-(p-chloro-N-cyclohexylbenzimidoyl)morpholine hydrochloride in each milliliter is prepared from the following ingredients:

| | |
|---|---|
| N-(p-chloro-N-cyclohexylbenzimidoyl)morpholine hydrochloride | 25 Gm. |
| Benzyl benzoate | 200 Gm. |
| Methylparaben | 1.5 Gm. |
| Propylparaben | 0.5 Gm. |
| Cottonseed oil q.s. | 1,000 ml. |

One milliliter of this sterile preparation is injected 4 times daily for the treatment of auricular fibrillation.

EXAMPLE 9

A sterile preparation suitable for intramuscular injection and containing 200 mg. of N-(p-chloro-N-cyclohexylbenzimidoyl)morpholine hydrochloride in each milliliter is prepared from the following ingredients:

| | |
|---|---|
| N-(p-chloro-N-cyclohexylbenzimidoyl)morpholine hydrochloride | 200 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected 4 times daily for treatment of ventricular fibrillation and retention of bodily fluids.

EXAMPLE 10

In the preceding Examples 4–9, an effective amount of compounds of Table I are compounded according to the methods of the Examples and are effectively employed in the manner of the Examples 4–9.

I claim:

1. A method for treating arrhythmic conditions in mammals which comprises systemically administering to a mammal in need of such treatment an anti-arrhythmic effective amount of a compound

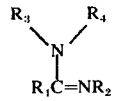

wherein $R_1$ and $R_2$ are the same or different and are selected from the group consisting of alkyl of one to eight carbon atoms, inclusive, cycloalkyl of from five to eight carbon atoms, inclusive, adamantyl, phenyl, phenalkyl, where alkyl is from one to three carbon atoms, inclusive, and mono and di-substituted phenyl and phenyl moiety of phenalkyl wherein the substituent(s) are the same or different and are selected from the group consisting of alkyl from one to three carbon atoms, inclusive, alkoxy of from one to three carbon atoms, inclusive, halogen, and trifluoromethyl; $R_3$ and $R_4$ taken together with the nitrogen atom to which they are attached, form morpholino and a pharmaceutically acceptable acid addition salt thereof in association with a pharmaceutical carrier.

2. A method in accordance with claim 1 wherein $R_1$ and $R_2$ are the same or different and are selected from the group consisting of alkyl of four to six carbon atoms, inclusive, cycloalkyl of from five to seven carbon atoms, inclusive, adamantyl, phenyl, phenalkyl, where alkyl is from one to three carbon atoms, inclusive.

3. A method in accordance with claim 1 where $R_1$ and $R_2$ are the same or different and are selected from the group consisting of cycloalkyl of five to seven carbon atoms, inclusive, and adamantyl.

4. A method in accordance with claim 1 where the administration is parenteral.

5. A method in accordance with claim 2 where the administration is parenteral.

6. A method in accordance with claim 3 where the administration is parenteral.

7. A method in accordance with claim 1 where the administration is oral.

8. A method in accordance with claim 2 where the administration is oral.

9. A method in accordance with claim 3 where the administration is oral.

10. A pharamaceutical composition which comprises an anti-arrhythmic effective amount of a compound

wherein $R_1$ and $R_2$ are the same or different and are selected from the group consisting of alkyl of one to eight carbon atoms, inclusive, cycloalkyl of from five to eight carbon atoms, inclusive, adamantyl, phenyl, phenalkyl, where alkyl is from one to three carbon atoms, inclusive, and mono and di-substituted phenvl and phenyl moiety of phenalkyl wherein the substituent(s) are the same or different and are selected from the group consisting of alkyl from one to three carbon atoms, inclusive, alkoxy of from one to three carbon atoms, inclusive, halogen, and trifluoromethyl; $R_3$ and $R_4$ taken together with the nitrogen atom to which they are attached, form morpholino and a pharmaceutically acceptable acid addition salt thereof in association with a pharmaceutical carrier.

11. A composition in accordance with claim 10 wherein $R_1$ and $R_2$ are the same or different and are selected from the group consisting of alkyl of four to six carbon atoms, inclusive, cycloalkyl of from five to seven carbon atoms, inclusive, adamantyl, phenyl, phenalkyl, where alkyl is from one to three carbon atoms, inclusive.

12. A composition in accordance with claim 11 wherein $R_1$ and $R_2$ are the same or different and are selected from the group consisting of cycloalkyl of five to seven carbon atoms, inclusive, and adamantyl.

13. A composition in accordance with claim 10 wherein the compound is N-(N,2-dicyclohexylacetimidoyl)morpholine.

14. A method in accordance with claim 1 wherein the compound is N-(N,2-dicyclohexylacetimidoyl)morpholine.

* * * * *